United States Patent [19]
Fukura et al.

[11] Patent Number: 5,638,951
[45] Date of Patent: Jun. 17, 1997

[54] PROBE COVER MOUNTING CASE

[75] Inventors: Masashi Fukura; Sigeru Makita, both of Kyoto; Mitsuru Kitamura, Kanagawa; Tadashi Ikeno, Kawasaki, all of Japan

[73] Assignee: OMRON Corporation, Kyoto, Japan

[21] Appl. No.: 668,720

[22] Filed: Jun. 24, 1996

Related U.S. Application Data

[63] Continuation of Ser. No. 267,628, Jun. 29, 1994, abandoned.

[30] Foreign Application Priority Data

Jun. 30, 1993 [JP] Japan ................................. 5-161648

[51] Int. Cl.⁶ .............................. B65D 85/38; B65H 3/00
[52] U.S. Cl. .............................. 206/306; 206/363; 221/25; 221/70
[58] Field of Search .............................. 206/306, 363, 206/389, 397, 398, 408, 409; 221/25, 56, 29, 70

[56] References Cited

U.S. PATENT DOCUMENTS

| | | | |
|---|---|---|---|
| 3,628,692 | 12/1971 | Blatz | 221/70 |
| 3,738,173 | 6/1973 | Sato | 206/306 X |
| 3,822,593 | 7/1974 | Oudewaal | 206/306 X |
| 4,197,944 | 4/1980 | Catlin | 206/306 |
| 4,457,633 | 7/1984 | Andrews | 206/306 X |
| 4,662,360 | 5/1987 | O'Hara et al. | 128/9 |
| 4,715,500 | 12/1987 | Heylen et al. | 206/397 |
| 4,911,559 | 3/1990 | Meyst et al. | 206/306 X |
| 5,088,834 | 2/1992 | Howe et al. | 374/158 |
| 5,100,018 | 3/1992 | Rosati et al. | 221/6 |
| 5,119,969 | 6/1992 | Haber | 221/25 X |

*Primary Examiner*—Bryon P. Gehman
*Attorney, Agent, or Firm*—Fish & Richardson P.C.

[57] ABSTRACT

A case for mounting on a probe of a radiation clinical thermometer a sheet shaped probe cover which includes a probe insertion member having an insertion opening to be inserted by the probe and an infection preventing sheet in contact with the probe insertion member. The case includes a cover storage portion for storing a series of continuing probe covers each having an engagement opening at a predetermined position thereof, a probe insertion cut portion for positioning each probe cover and for insertion by the probe, a support surface disposed around the probe insertion cut portion to support a peripheral of the insertion opening of the probe insertion member of one of the probe covers, and a projection adapted to be engaged with the engagement opening of a subsequent probe cover when the probe cover mounted on the probe is torn at the probe insertion cut portion.

9 Claims, 12 Drawing Sheets

PROBE COVER MOUNTING CASE

This application is a continuation of U.S. application Ser. No. 08/267,628, filed Jun. 29, 1994, now abandoned.

BACKGROUND OF THE INVENTION

1. Field of the Invention

This invention relates to a case for housing a probe cover to be mounted on a probe, and more particularly to an improved case for mounting a cover on a probe of a sensor.

2. Discussion of the Related Art

A conventional radiation clinical thermometer having a probe for measuring body temperature by sensing infrared energy from an ear opening of a patient employs a probe cover mounted on the probe to be inserted into the ear opening for measurement. This prevents the probe from being contaminated. For this purpose, the probe cover must be replaced with a new one whenever a body temperature is measured. The frequent replacement is done for health purposes.

Conventional examples of probe covers and a probe cover case enclosing the prove covers is shown in FIGS. 12 through 16.

In FIGS. 12, a plurality of conical probe covers 71 are piled up to be enclosed within a case 70 as shown in U.S. Pat. No. 5,088,834. One of covers 71 is mounted on a probe by inserting the probe into the piled up covers. This construction has the disadvantage that two or more covers are simultaneously mounted on the probe because the piled up covers are not individually separated. If a plurality of covers are mounted on the probe, the covers are required to be remounted by hands which invites problems in health because the covers are directly touched by hands. This prevents smooth measurement when a series of measurements are required.

In FIG. 13, a plurality of conical probe covers 81 are arranged in parallel to be enclosed within a case 80 as shown in U.S. Pat. No. 4,662,360. One of probe covers 81 is mounted on a probe by inserting the probe into the covers 81. This construction avoids such inconvenience that a plurality of covers are simultaneously mounted on the probe, but has the disadvantages that only small number of covers can be enclosed in comparison with the whole volume of the case because of broad spacing between the neighboring covers or in a portion to be inserted by the probe, whereby the frequency of operation for enclosing covers into the case is increased with deteriorating the operation efficiency when many times of measurements are required to be executed continuously. If a large number of covers are desired to be enclosed in the case, the case becomes bulky and inconvenient for carriage.

FIGS. 14 and 15 illustrate another example of a probe cover case, in which a probe cover is mounted in the order of illustrations of FIG. 14(a) and (b) and FIG. 15(c) and (d). In this probe cover case, a plurality of probe covers are continued in series as a rolled sheet W and enclosed in a case 90 to be mounted on a probe 100 by a predetermined mounting operation.

The mounting operation will be described in detail hereinafter. Case 90 includes a lid provided with a probe insert hole 91 for an open-and-close movement and a hold member 93 to enclose the rolled covers W. In order to mount a cover on probe 100 by using the case, one piece of cover C is pulled up from the rolled covers W to be placed on lid 92 adjusting a ring of cover C to probe insert hole 91 in position as shown in FIG. 14(a). In FIG. 14(b), as probe 100 is inserted into hole 91, it is covered with cover C. As probe 100 is pulled up from hole 91 after such mounting, cover C is pulled up until a perforation of a subsequent cover C' comes near an edge of lid 92 as shown in FIG. 15(c). Then, as cover C' is held by hold member 93 in FIG. 15(d) and probe 100 is pulled outwardly of case 90, cover C is separated from cover C' in the perforation and simultaneously the subsequent cover C' is placed on lid 92.

A cover case constructed in this manner can overcome the inconvenience of a plurality of covers simultaneously mounted on probe and provide a large number of covers to be enclosed within a compact case because of a rolled cover sheet. The operation of the case, however, is not convenient. The probe must be inserted into hole 91 after adjusting the ring of probe cover into hole 91, and hold member 93 must be pressed against the subsequent cover C' for separating cover C. This operation is more complicated than the above-mentioned conventional operations, and difficult to provide smooth measurements continuously made many times.

SUMMARY OF THE INVENTION

It is, therefore, a primary object of this invention to provide an improved case for housing a probe cover to be mounted on a probe of a radiation thermometer, which provides a smooth and ensured supply of probe covers keeping an easy mounting operation and health and is of a reduced size to be portable within a hand of human being.

According to a first aspect of this invention, there is provided a case for mounting sheet shaped probe covers on a probe of a radiation clinical thermometer which include a probe insertion member having an insertion opening to be inserted by the probe and an infection preventing sheet in contact with the probe insertion member, which includes a cover storage portion for storing a series of continuing probe covers each having an engagement opening at a predetermined position thereof, a probe insertion cut portion for positioning each probe cover and for insertion by the probe, a support surface disposed around the probe insertion cut portion to support a peripheral of the insertion opening of the probe insertion member of one of the probe covers, and a projection adapted to be engaged with the engagement opening of a subsequent probe cover when the probe cover mounted on the probe is torn at the probe insertion cut portion.

In this probe cover case, as a probe is inserted into the probe insertion cut portion, the first probe cover which is previously fixed to the probe insertion cut portion in position is mounted on the probe. As the probe is moved from the probe insertion cut portion in a horizontal direction, the cover is pulled out together with the probe and an insertion opening of a probe insertion member of a subsequent cover comes to the probe insertion cut portion, wherein the projection of the case comes into an engagement opening of the probe cover for engagement therewith and the subsequent cover stops when the insertion hole of the probe insertion member comes into the position of the probe insertion cut portion. Upon further movement of the probe to the horizontal direction, the mounted cover can be separated by breaking a weaken portion (perforations) formed between neighboring covers because the subsequent cover is held by the projection.

Its subsequent mounting operations are just to insert the probe into the probe insertion hole and to move the probe covered with the cover in a horizontal direction because the probe insertion openings of subsequent covers are subsequently brought into the fixed position of the probe insertion cut portion.

According to a second aspect of this invention, there is provided a probe cover case, in which the engagement opening disposed in the predetermined portion of the above-mentioned cover is an insertion opening for the probe insertion member, and the above-mentioned projection is so movably biased to appear on the probe insertion cut portion from the inside of the case, to be prossed backward by the probe inserted into the probe insertion cut portion, and to again appear so as to come into contact with the peripheral of insertion hole of the probe insertion member when the probe cover mounted on the probe is broken off.

In this probe cover case, as the probe is inserted into the probe insertion cut portion, the cover previously positioned at the probe insertion cut portion is mounted on the probe. At this moment the projection appearing on the probe insertion cut portion is pushed backward by the probe. As the probe is moved in a horizontal direction, the cover is pulled and comes out of the projection to return to its original position. Upon further movement of the probe the projection comes into the insertion opening of a probe insertion member of the subsequent probe cover for engagement with the peripheral of the insertion opening. The subsequent cover is held in a fixed position by the engagement of the insertion opening peripheral with the projection, so that the cover mounted on the probe can be separated from the perforation.

After such separation, a peripheral of an insertion opening of a probe insertion member of its subsequent cover is engaged with the projection at the probe insertion cut portion, so that subsequent mounting operations can be done by only inserting the probe into the probe insertion cut portion and moving the probe in a horizontal direction.

In the probe cover case according to the first and second aspects of this invention, the supply of probe covers can be smoothly and firmly executed, and the case has only to have a minimum members such as a cover storage, a probe insertion cut portion, a support surface, a projection and so forth and can be reduced to a hand held size.

According to a third aspect of this invention, there is provided an improvement of the probe cover case in accordance with the second aspect of the invention, in which the peripheral of probe insertion member of the probe cover has a stiffness in comparison with other portion than the peripheral.

In this improved probe cover, when the subsequent cover is set to the probe insertion cut portion by moving the probe in a horizontal direction after mounting the cover on the probe, the peripheral of the opening of the probe insertion member is positioned in a slant direction due to its stiffness, a front edge of the peripheral rides over the projection appearing on the probe insertion cut portion, the peripheral becomes in a horizontal position when the projection confronts to the insertion opening, whereby the opening is penetrated by the projection and the projection is easily engaged with a rear edge of the peripheral. Thus, the positioning of the subsequent cover is further ensured.

According to a fourth aspect of this invention, there is provided an improvement of the probe cover case in accordance with the first aspect of this invention, which includes a probe guide in addition to the cover storage, the probe insertion cut portion, and the supporting surface. The probe guide is movably so disposed in the prove cover case to oppose to the probe insertion cut portion, to provide a probe insertion hole with a base end of the cut portion, and to be driven backward when the probe covered with the probe cover is moved in a horizontal direction from the cut portion.

According to the case of the fourth aspect, the probe guide provides a probe insertion hole with a base end of the cut portion when a probe is inserted into the probe insertion cut portion, and is driven back by the probe when the probe mounted by the probe cover is moved in a horizontal direction from the probe insertion cut portion. As the mounted cover is separated, the probe guide is returned to the position opposite to the probe insertion cut portion.

The probe cover employed in a case according to this invention may be any cover in a sheet which consists of a probe insertion member having a probe insertion opening and an infection preventing sheet connected with the insertion member. Accordingly, various kinds of covers may be employed about their materials and forms. As described in the embodiments, a cover for the case according to this invention consists of a ring to be inserted by a probe, a support sheet for supporting the ring and including at its portion within the ring an opening having a same diameter as an opening of the ring, an infection preventing sheet disposed on a ring side or its opposite side of the ring support sheet. In this cover, the probe insertion member is constructed by the ring and the ring support sheet, the ring opening corresponds to an insertion opening, and a ring width corresponds to a insertion opening peripheral. The ring opening is desirable to correspond to an engaging opening.

BRIEF DESCRIPTION OF THE DRAWINGS

Other objectives and advantages of this invention will be more readily apparent from the following detailed description provided in conjunction with the following figures, of which.

DETAILED DESCRIPTION OF THE INVENTION

Figure 1:
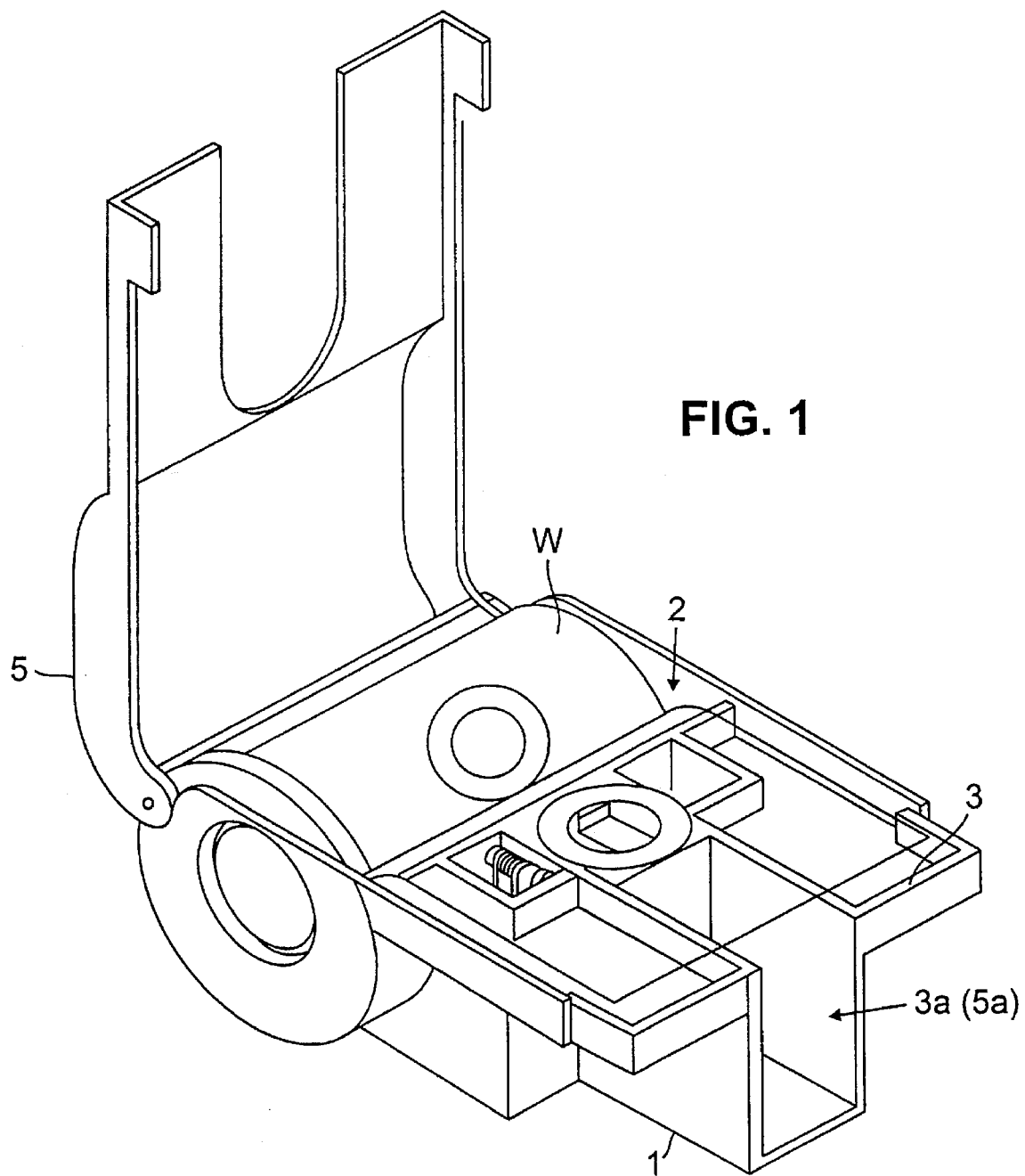
FIG. 1 is a perspective view of a case for a probe cover as a preferred embodiment of this invention.
Figure 2:
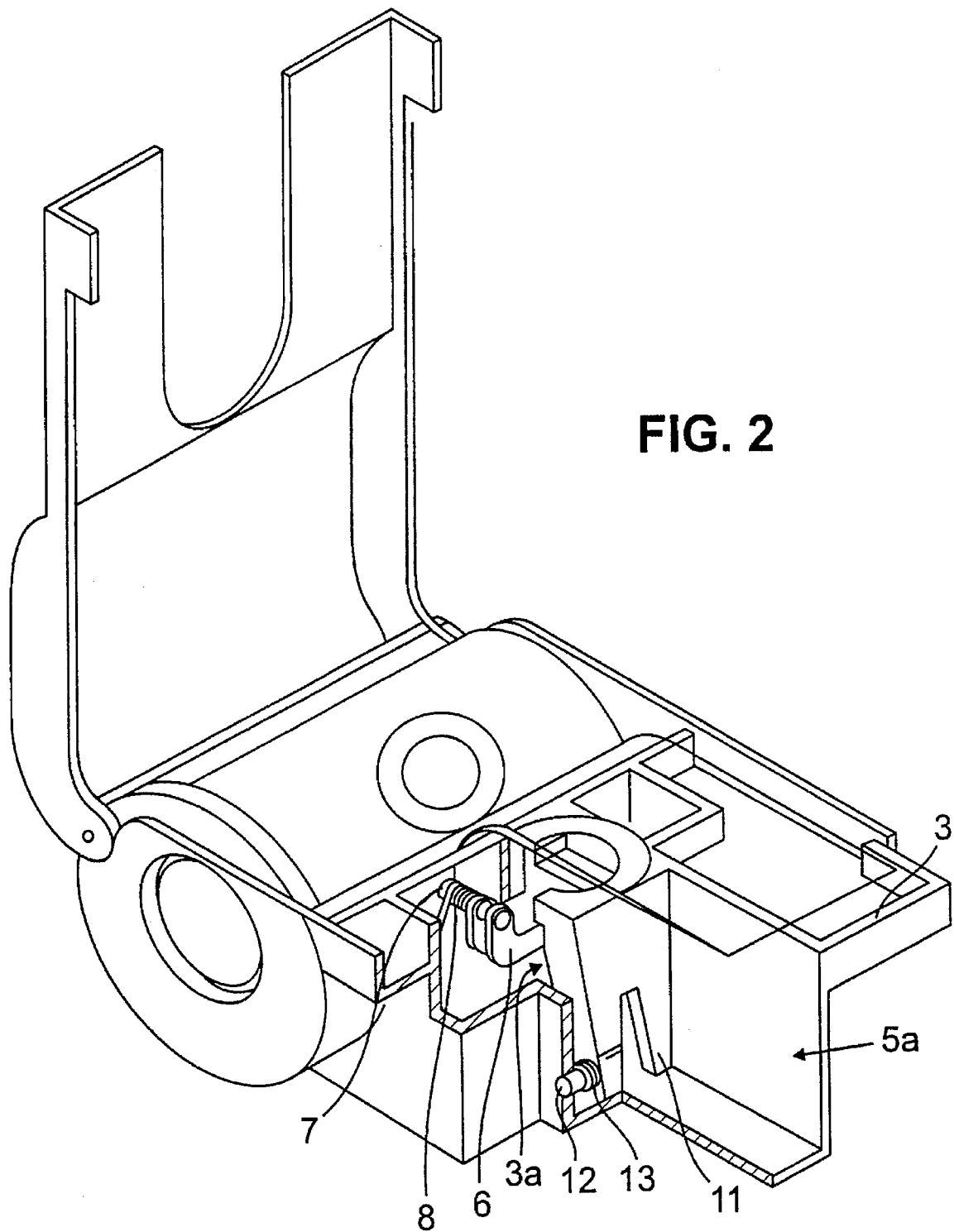
FIG. 2 is a perspective partial view of the case of FIG. 1.
Figure 3:
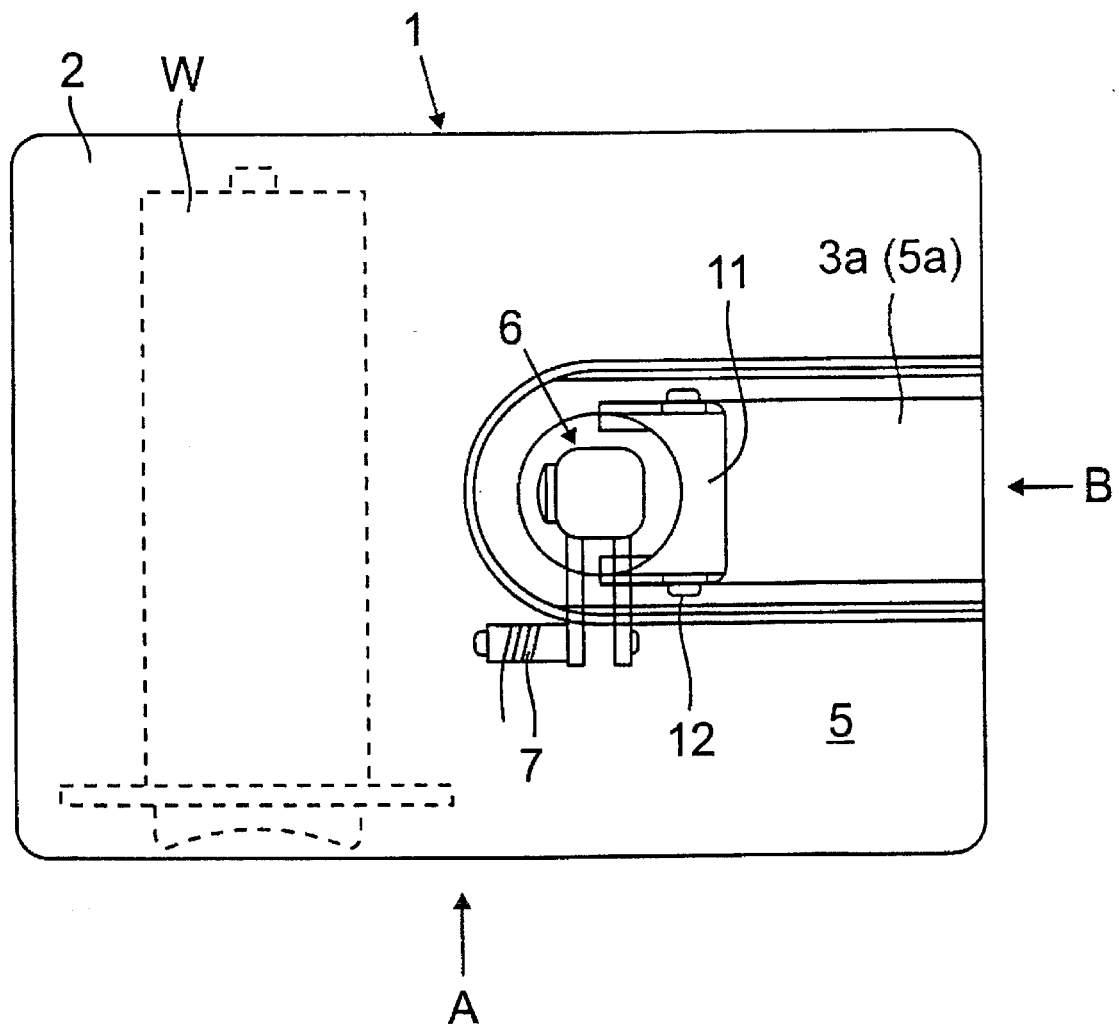
FIG. 3 is a plan view of the case of FIG. 1.
Figure 4:
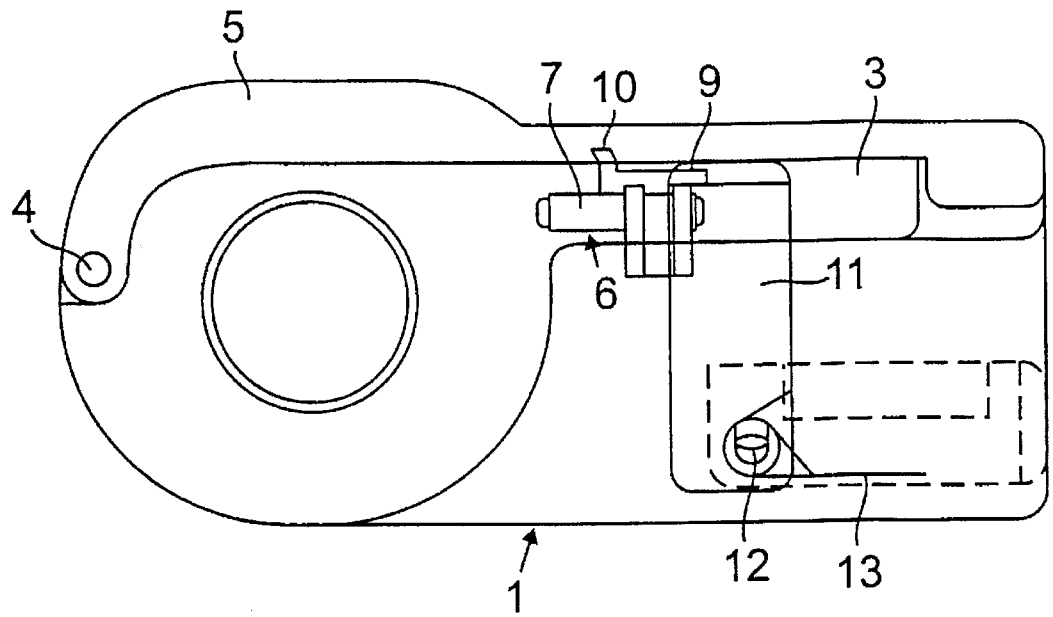
FIG. 4 is a side view of the case in view of a direction A of FIG. 3.
Figure 5:
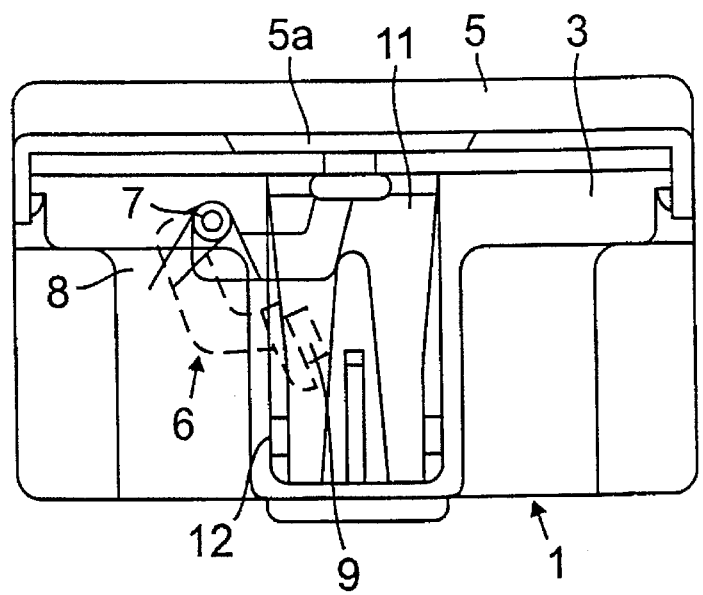
FIG. 5 is a side view of the case in view of a direction B of FIG. 3.

Referring now to FIG. 1, there is shown a perspective view of a cover case 1 at its storage 2 for enclosing rolled covers W as a preferred embodiment of this invention. For explanation of the case, FIG. 2 shows a perspective partial view of the case, FIG. 3 shows a plan view of the case of FIG. 1, FIG. 4 shows a side view of the case in view of a direction A of FIG. 3, and FIG. 5 shows a side view of the case in view of a direction B of FIG. 3.

Figure 10:
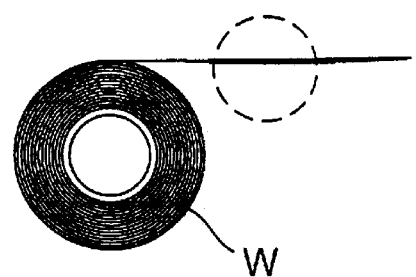
FIG. 10 is a side view of rolled covers to be stored in the case of FIG. 1.
Figure 11:
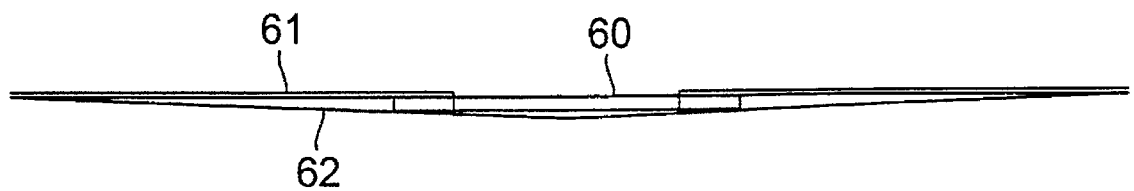
FIG. 11 is an enlarged view of the cover marked with a one dotted circle line of FIG. 10.
Figure 12:
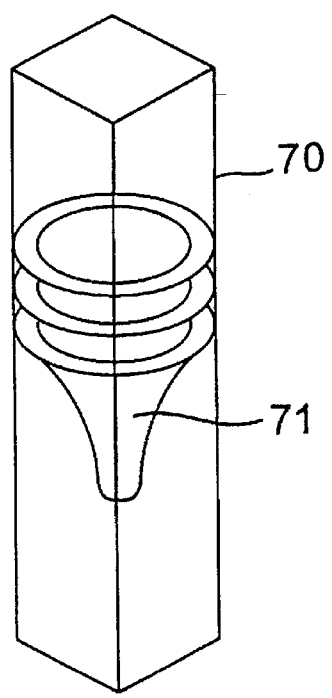
FIG. 12 is a perspective view of a conventional case enclosing covers.
Figure 13:
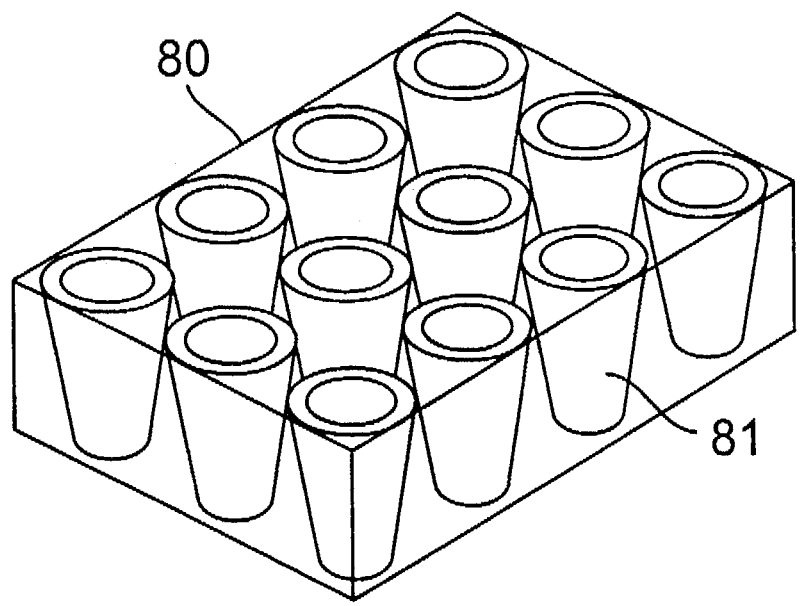
FIG. 13 is a perspective view of another conventional case enclosing covers.
Figure 14:
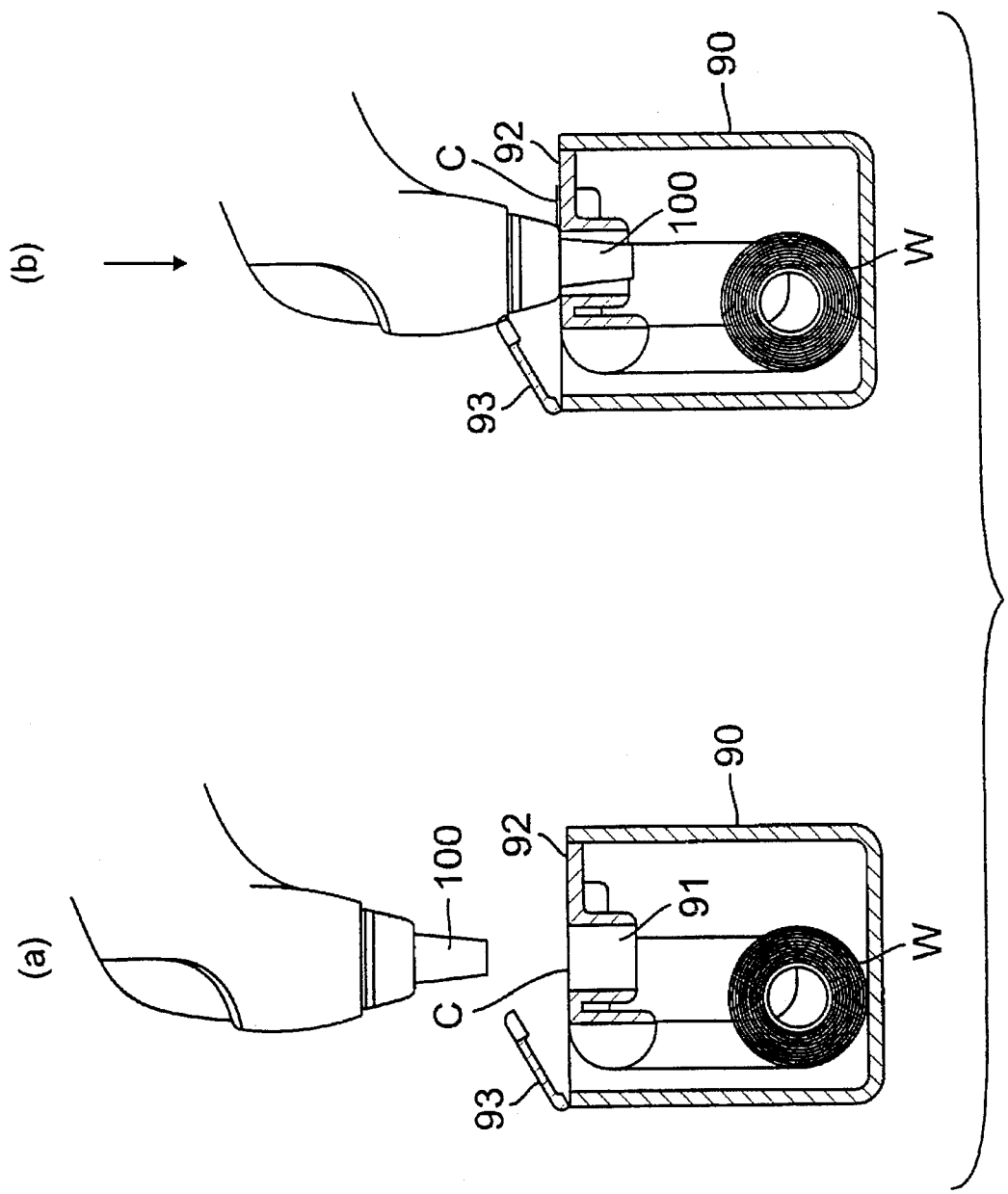
FIG. 14 is an illustration for mounting a cover on a strobe by employing conventional case and covers.
Figure 15:
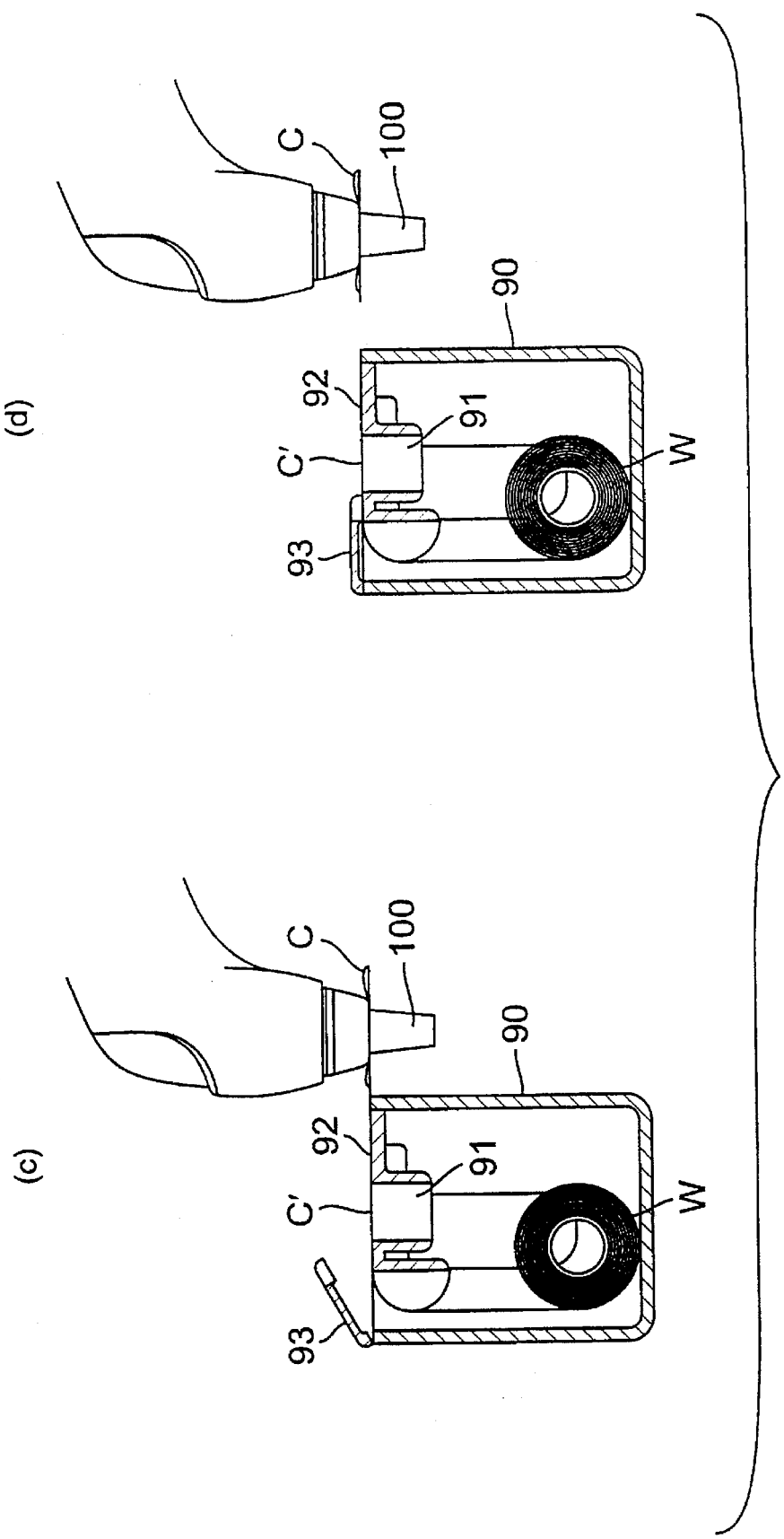
FIG. 15 is a subsequent illustration of FIG. 14 for mounting the cover.

The rolled covers W are a roll of a sheet consisting of a series of probe covers each having a ring, a sheet for supporting the ring, and an infection preventing sheet as shown in FIG. 10. An enlarged side view of a cover in FIG. 10 is shown in FIG. 11. The cover consists of a ring 60 which is adapted to be inserted by a probe, to come to engagement with a base end of the probe and to serve as an engagement opening, a ring support sheet 61 for supporting ring 60 which has an opening having a similar diameter to the ring at its position corresponding to the ring, and an infrared-transparent and infection-preventing sheet 62 disposed on ring support sheet 61 across ring 60. Ring 60 has a larger stiffness than sheets 61 and 62. Sheets 61 and 62 are wound around a roll core to make a roll to be enclosed in storage 2 of case 1, in which sheet 61 is on an external side of the roll and sheet 62 is on an internal side of the roll.

Returning to FIGS. 1 to 5, case 1 includes a plate 3 and a lid 5 supported by a shaft 4 (FIG. 4) for a open-and-close movement. The plate and the lid include U shaped cut portions 3a and 5a respectively (FIG. 3), each having an enough width for inserting a probe of a radiation clinical thermometer. A cover extending from the roll stored in storage portion 2 extends through a slit between plate 3 and lid 5, and the ring of the cover is supported by a support wall disposed at a peripheral of cut portion 3a of plate 3 (FIG. 2). Thus, by inserting the probe in probe insertion cut portions 3a and 5a, the probe can be easily inserted within the ring supported by the support wall of plate 3.

In case 1, a lever 6 at its one end is swingably supported by a shaft 7, a spring 8 is mounted on shaft 7 to bias lever 6 upward of case 1. On other end of lever 6 there is disposed a nail 9 having at an upper end a flat wall and a projection 10. When lever 6 is thoroughly biased upward of case 1 by spring 8, nail 9 appears from inside of case 1 toward a base end of probe insertion cut portions 3a and 5a of plate 3 and lid 5, and projection 10 slightly projects from cut portion 3a (FIG. 4). Lever 6 is easily depressed by the probe against the biassing force by spring 8 (FIG. 5).

Inside of case 1 there is disposed a probe guide 11 having a U shaped cross section. Probe guide 11 at its one end is swingably supported by a shaft 12 which is mounted by a coil spring 13 so as to bias probe guide 11 upward of case 1. As probe guide 11 is thoroughly biased upward by spring 13, guide 11 confronts nail 9 of lever 6 and provides a probe insertion hole with base ends of cut portions 3a and 5a for probe insertion (FIG. 3). Probe guide 11 easily falls down against the biasing force of spring 13 as it slides in a horizontal direction along cut portions 3a and 5a (FIG. 4).

Returning to FIGS. 6 to 9, there is shown illustration for mounting a probe cover on a probe of a clinical radiation thermometer by employing case 1.

Figure 6:
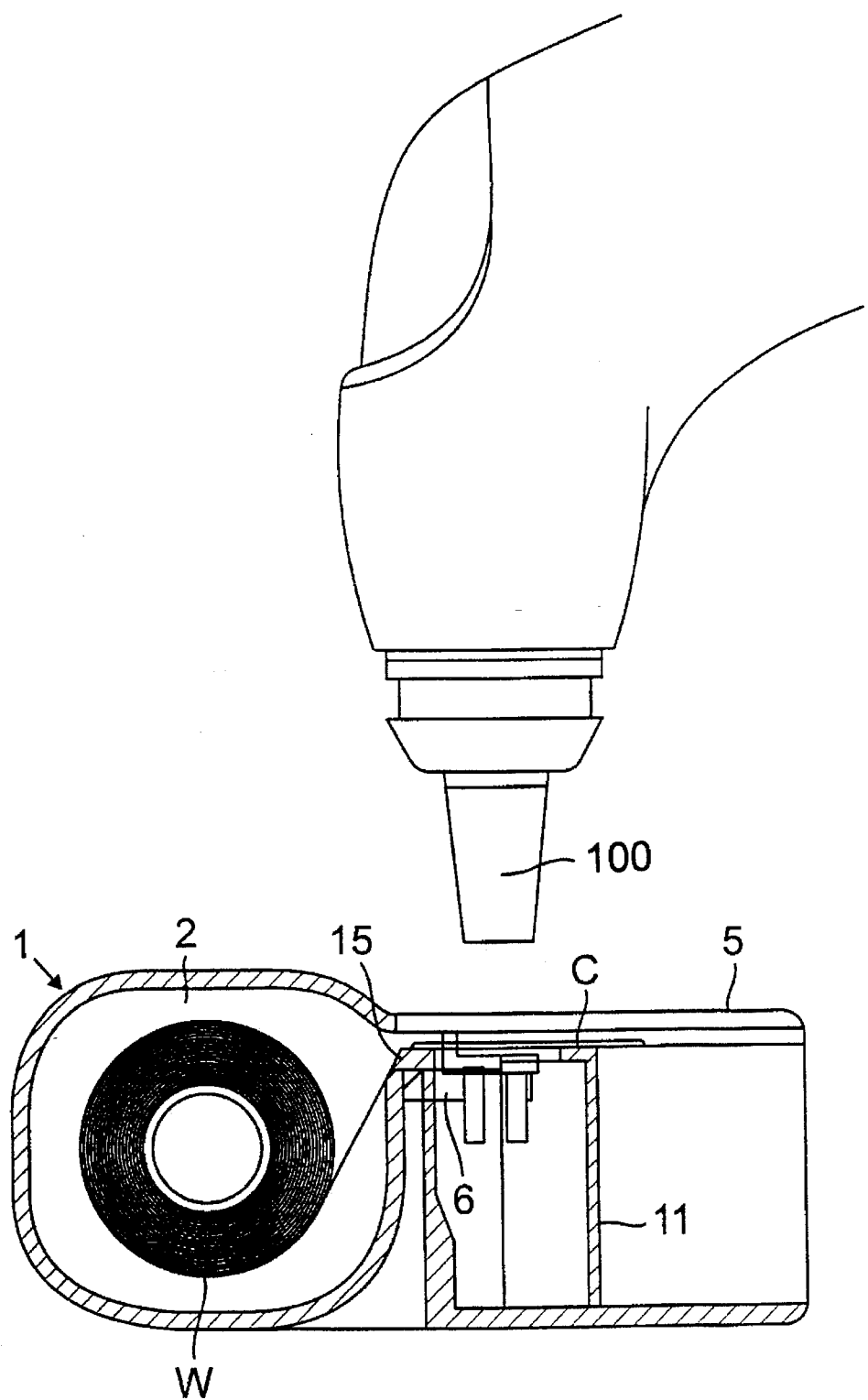
FIG. 6 is an illustration for mounting a cover on a probe by employing the case.

In FIG. 6, the above-mentioned rolled covers W is enclosed in storage portion 2 of case 1, only the first cover C is set to a predetermined position of a base end of probe insertion cut portion 3a of plate 3, via., a position where nail 9 of lever 6 appears. As lid 5 is closed, cut portions 3a and 5a of plate 3 and lid 5 overlaps, cover C is positioned between plate 3 and lid 5, and a ring of cover C is supported by a supporting surface of a peripheral of cut portion 3a. Then, lever 6 and probe cover 11 are biased upward by springs 8 and 13 respectively.

Figure 7:
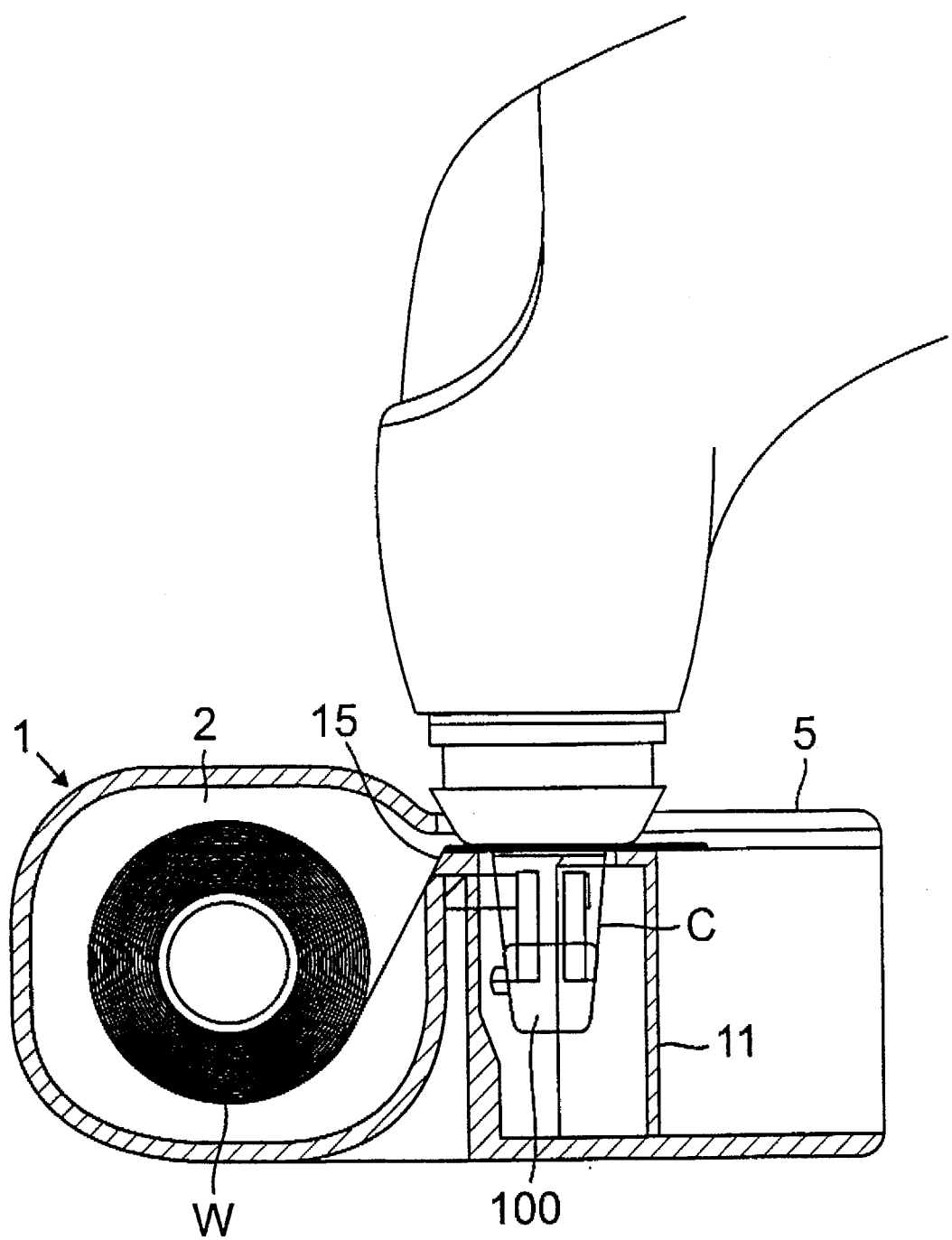
FIG. 7 is a subsequent illustration of FIG. 6 for mounting the cover on the probe.

After completion of setting covers, probe 100 is inserted into a probe insertion hole provided by probe guide 11 and base ends of cut portions 3a and 5a as shown in FIG. 7, in which probe 100 is guided by probe guide 11. Accordingly, nail 9 of lever 6 is depressed by probe 100 and lever 6 is displaced downward of case 1. Simultaneously, probe 100 inserted within the ring of cover C is mounted by cover C.

Figure 8:
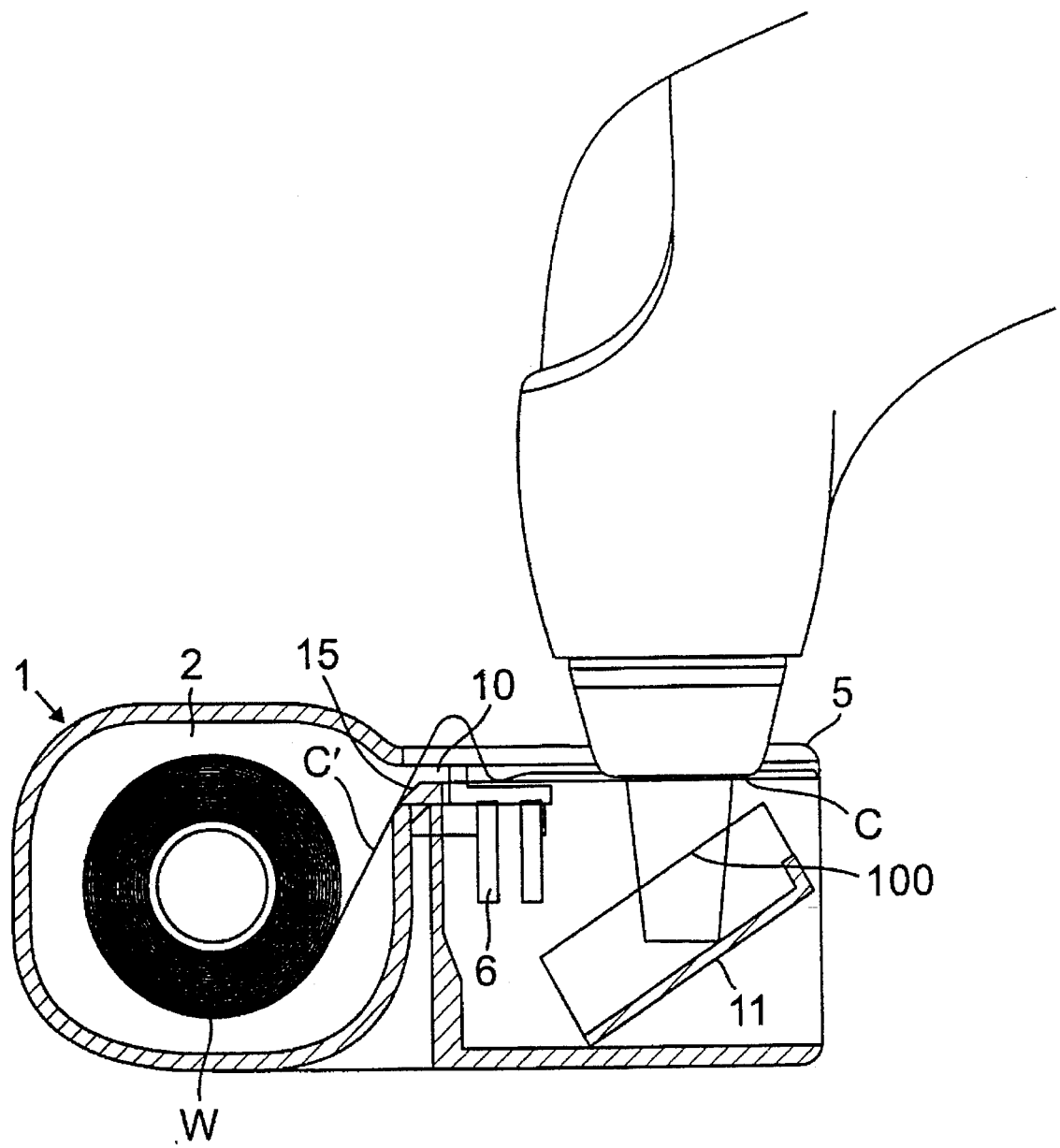
FIG. 8 is a subsequent illustration of FIG. 7 for mounting the cover.

After mounting of cover C, probe 100 is slid in a horizontal direction along cut portions 3a and 5a as shown in FIG. 8. As probe 100 is slid, probe guide 11 falls down to a lower portion of case 1, and probe 100 is released from nail 9 of lever 6 whereby lever 6 is returned to its original position by spring 8 and projection 10 of nail 9 projects from cut portion 3a.

As probe 100 is slid, a subsequent cover C' is withdrawn from the rolled covers W, but cover C' contacts an edge 15 of storage 2 when it moves out from storage 2. Then, a front edge of ring 60 of the cover C' is raised due to its larger stiffness than sheet 61 and 62 (FIG. 11). When cover C' further moves and the front edge exceeds projection 10, a rear edge of the ring passes through edge 15 of storage 2 and cover C' becomes in a horizontal state. Then, projection 10 raises sheet 62 to project from the ring of cover C'.

Figure 9:
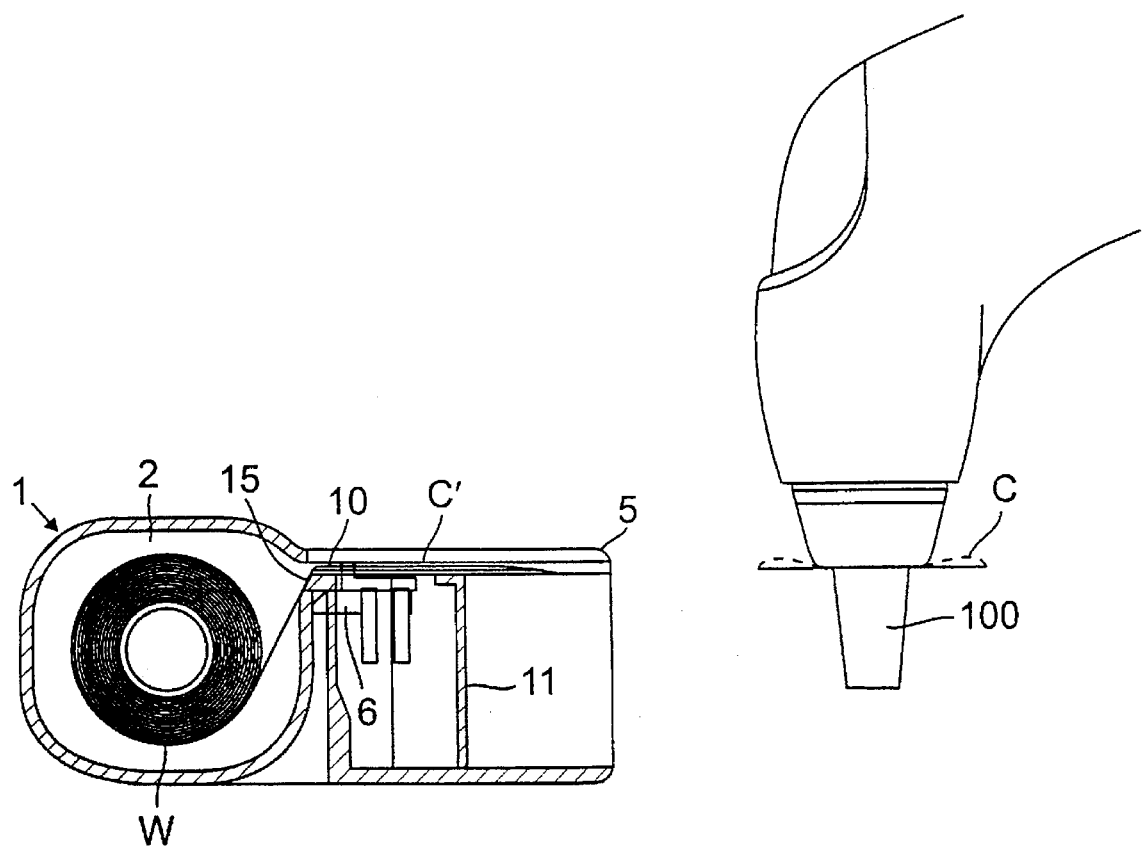
FIG. 9 is a subsequent illustration of FIG. 8 for mounting the cover.

As probe 100 is moved from cut portions 3a and 5a to an exit as shown in FIG. 9, projection 10 comes into engagement with a rear edge of a ring of cover C' and the withdrawal movement of cover C' stops. Then, cover C' mounted on probe 100 is torn at porforations between covers C and C' by a withdrawal force, so that probe 100 mounted by cover C can be completely pulled out of case 1 and at the same time probe guide 11 returns to its original position by spring 13.

Moreover, subsequent cover C' at its ring is engaged with projection 10, whereby positioning operation is automatically finished and it is not necessary to intentionally position each subsequent cover to a predetermined position. Accordingly, subsequent mounting operations of covers can be done only by repeating the operation for inserting the probe into insertion hole and for moving the probe in a horizontal direction, whereby cover mounting operation is simplified and supply of covers to the probe is smoothly assured.

It should be understood that the above description is merely illustrative of this invention and that many changes and modifications may be made by those skilled in the art. Particularly the configuration of the lever having nail and projection and probe guide according to this invention is not limited to the above-described embodiment. The plate, the lid and the probe insertion cut portion may be modified if desired. Moreover, the case according to this invention can be applied to other covers than that of the above embodiment.

What is claimed is:

1. A case for mounting a sheet shaped probe cover on a probe of a radiation clinical thermometer, said probe cover including a probe insertion member having an insertion opening to be inserted by the probe and an infection preventing sheet in contact with the probe insertion member, said case comprising:

a probe cover storage portion for storing a series of continuing probe covers each having an insertion opening at a predetermined position thereof, a probe insertion cut portion for positioning each probe cover and for insertion by the probe, a support surface disposed around said probe insertion cut portion to support a peripheral part of the insertion opening of the probe insertion member of one of said probe covers, and a projection adapted to be pushed by the probe inserted into the insertion opening to be disengaged from the insertion opening and to be engaged with the insertion opening of a subsequent probe cover when the probe cover mounted on a probe is separated from the subsequent probe cover at said probe insertion cut portion.

2. A case according to claim 1, in which said insertion opening disposed in the predetermined portion of said probe cover is an insertion opening of said probe insertion member, and said projection is movably biased to appear on the probe insertion cut portion from the inside of the case, to be pressed backward by the probe inserted into the probe insertion cut portion, and to again appear so as to come into contact with the peripheral of insertion opening of the probe insertion member when the probe cover mounted on a probe is separated from the subsequent probe cover.

3. A case according to claim 1 in combination with a probe cover, in which a peripheral of the probe insertion member of said probe cover has a larger stiffness than the probe insertion member and the infection preventing sheet.

4. A case according to claim 1, in which said probe cover storage portion is large enough to store a plurality of continuing probe covers.

5. A case for mounting a sheet shaped probe cover on a probe of a radiation clinical thermometer, said probe cover including a probe insertion member having an insertion opening to be inserted by the probe and an infection preventing sheet in contact with the probe insertion member, said case comprising:

a probe cover storage portion for storing a series of continuing probe covers, a probe insertion cut portion for positioning each probe cover and for insertion by the probe, a support surface disposed around said probe insertion cut portion to support a peripheral of the insertion opening of the probe insertion member of one of said probe covers, and a probe guide movably disposed in opposition to the probe insertion cut portion to provide a probe insertion hole with a base end of the probe insertion cut portion, and to be driven backward when the probe covered with the probe cover is moved in a horizontal direction from the probe insertion cut portion.

6. A method for mounting a series of sheet shaped probe covers on a probe of a radiation clinical thermometer, each of said probe covers including a probe insertion member having an insertion opening to be inserted by the probe and an infection preventing sheet in contact with the probe insertion member, by employing a cover which includes a probe cover storage portion for storing a series of continuing probe covers each having an insertion opening at a predetermined position thereof, a probe insertion cut portion for positioning each probe cover and for insertion by the probe, a support surface disposed around said probe insertion cut portion to support a peripheral of the insertion opening of the probe insertion member of one of said probe covers, and a projection adapted to be pushed by the probe inserted into the insertion opening to be disengaged from the insertion opening and to be engaged with the insertion opening of a subsequent probe cover when a probe cover mounted on the probe is separated from the subsequent probe cover at the probe insertion cut portion, comprising the steps of inserting the probe into said probe insertion cut portion of said case, mounting said probe cover on the probe by pushing the probe, moving said probe along said supporting surface, and separating said probe cover when the subsequent probe cover is positioned at a predetermined position.

7. A case for mounting a sheet shaped probe cover on a probe, said probe cover including a probe insertion member having an insertion opening to receive an inserted probe and a sheet in contact with the probe insertion member, said case comprising:

a probe cover storage portion for storing a series of continuing probe covers each having an insertion opening at a predetermined position thereof a probe insertion cut portion for positioning each probe cover and for insertion by the probe, a support surface disposed around said probe insertion cut portion to support a peripheral of the insertion opening of the probe insertion member of one of said probe covers, and a projection adapted to be pushed by the probe inserted into the insertion opening to be disengaged from the insertion opening and to be engaged with the insertion opening of a subsequent probe cover when a probe cover mounted on the probe is separated from the subsequent probe cover at said probe insertion cut portion.

8. A method of mounting a series of probe covers on a probe, each of said probe covers including a probe insertion member having an insertion opening to receive an inserted probe and sheet in contact with the probe insertion member, by employing a cover which includes a probe cover storage portion or storing a series of continuing probe covers, a probe insertion cut portion for positioning each probe cover and for insertion by the probe, a support surface disposed around said probe insertion cut portion to support a peripheral of the insertion opening of the probe insertion member of one of said probe covers, and a projection adapted to be pushed by the probe inserted into the insertion opening to be disengaged from the insertion opening and to be engaged with the insertion opening of a subsequent probe cover when a probe cover mounted on the probe is separated from the subsequent probe cover at the probe insertion cut portion, the method comprising the steps of:

inserting the probe into said probe insertion cut portion of said case, mounting said probe cover on the probe by pushing the probe, moving said probe along said supporting surface, and separating said probe cover when the subsequent probe cover is positioned at a predetermined position.

9. A case for mounting a sheet shaped probe cover on a probe of a radiation clinical thermometer, said probe cover including a probe insertion member having an insertion opening to be inserted by the probe and an infection preventing sheet in contact with the probe insertion member, said case comprising:

a probe cover storage portion for storing a series of continuing probe covers each having an insertion opening at a predetermined position thereof, a probe insertion cut portion for positioning each probe cover and for insertion by the probe, a support surface disposed around said probe insertion cut portion to support a peripheral of the insertion opening of the probe insertion member of one of said probe covers, and a stopper adapted to be engaged with a subsequent probe cover so that the subsequent probe cover does not move when a probe cover mounted on the probe is separated at said probe insertion cut portion.

* * * * *